United States Patent [19]

Photis

[11] 4,234,507
[45] Nov. 18, 1980

[54] PROCESS FOR PREPARING CYANOHYDRIN ESTERS

[75] Inventor: James M. Photis, Ridgefield, Conn.

[73] Assignee: Stauffer Chemical Company, Westport, Conn.

[21] Appl. No.: 80,956

[22] Filed: Oct. 1, 1979

[51] Int. Cl.³ ............... C07C 121/38; C07C 121/46; C07C 121/75
[52] U.S. Cl. ............................ 260/465 D; 260/464; 260/465.4
[58] Field of Search ................. 260/465 D, 464, 465.4

[56] References Cited

U.S. PATENT DOCUMENTS 4,113,763  9/1978  Norton ........................... 260/465 D

FOREIGN PATENT DOCUMENTS 52-142046  11/1977  Japan.

OTHER PUBLICATIONS

Cox et al., *Organic Synthesis Collective*, vol. 2, p. 7 (1943).
Wagner et al., *Organic Synthesis Collective*, vol. 3, p. 324 (1955).
Nasipuri et al., *J. Indian Chemical Society*, 44, p. 556 (1967).
Gassman et al., *Tetrahedron Letters*, pp. 3773-3776 (1978).
Umino et al., *Tetrahedron Letters*, No. 33, pp. 2875-2876 (1976).
Sugimoto et al., *J. Chem. Soc. Chem. Comm.*, pp. 926-927 (1978).
Kinishi et al., *Agric. Biol. Chem.*, 42 (4), pp. 869-872 (1978).
Borch et al., *J. Org. Chem.*, 37, pp. 726 (1972).

*Primary Examiner*—Dolph H. Torrence
*Attorney, Agent, or Firm*—William C. Gerstenzang

[57] ABSTRACT

Cyanohydrin esters are prepared by reacting an acyl halide represented by the structure

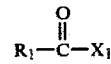

with an acyl halide represented by the structure

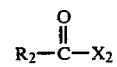

an alkali metal cyanide and an alkali metal borohydride.

9 Claims, No Drawings

PROCESS FOR PREPARING CYANOHYDRIN ESTERS

BACKGROUND OF THE INVENTION

The present invention relates to a novel process for the preparation of cyanohydrin esters. More particularly, the present invention relates to the preparation of cyanohydrin esters from acyl halides.

Cyanohydrin esters are important industrial materials both as intermediates to be used in making other compounds and as compounds having utility in and of themselves.

An example of the former is meta-phenoxybenzaldehyde cyanohydrin acetate, which is represented by the formula:

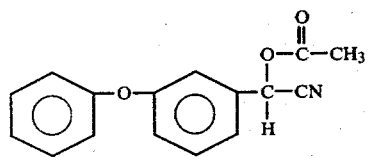

An example of the latter is the pyrethroid-type insecticide represented by the formula:

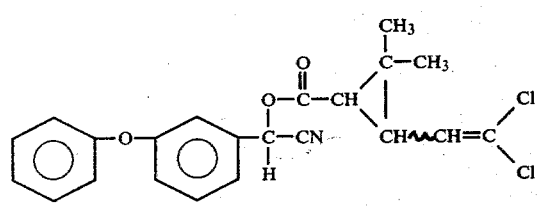

The compound of formula I can be used as an intermediate cyanohydrin ester from which the insecticidally-active cyanohydrin ester of formula II is prepared, as follows:

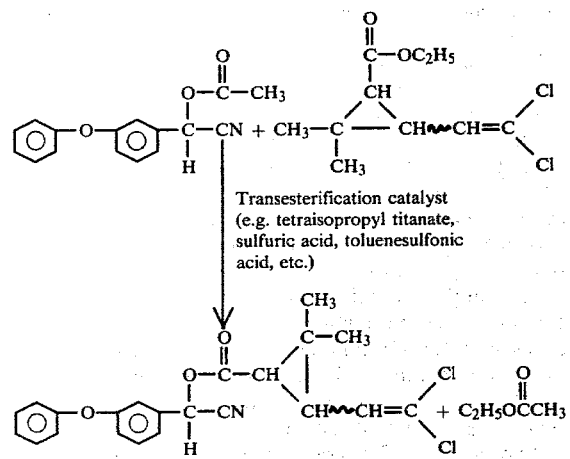

This method of preparing cyanohydrin esters of the type represented by compound II presupposes the availability of the intermediate compound I.

The intermediate cyanohydrin ester represented by formula I can be prepared by reacting a free cyanohydrin with acetic anhydride, as follows:

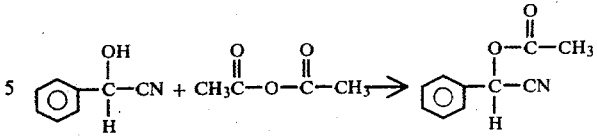

This overall method for preparing cyanohydrin esters of the type represented by formula II is not preferred for two reasons. The first is that it is a two-step process, the first step being the preparation of an intermediate cyanohydrin ester (compound I), and the second step being the further reaction of the intermediate to form the final product. The second objection is that it requires, in the first step, the handling of a free cyanohydrin. Free cyanohydrins are unstable compounds which can release HCN.

It is highly desirable therefore that a method be provided for preparing cyanohydrin esters by a one-step process which does not require the use of free cyanohydrins.

SUMMARY OF THE INVENTION

It is an object of the present invention to provide a novel one-step process in which cyanohydrin esters are prepared directly from acyl halides.

It has now been discovered that cyanohydrin esters can be readily prepared directly from acyl halides by reacting the acyl halides with an alkali metal cyanide and an alkali metal borohydride.

The reaction is preferably carried out under conditions of phase transfer catalysis.

This discovery is particularly surprising in view of the knowledge that acyl chlorides and sodium cyanides usually react under phase transfer conditions to form a mixture of a dimer and an acyl cyanide, as follows:

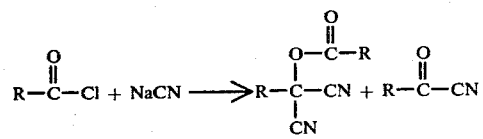

In accordance with the present invention there is provided a process for preparing cyanohydrin esters represented by the formula:

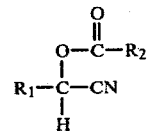

which comprises reacting at least one acyl halide represented by the structure:

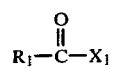

with at least one acyl halide represented by the structure:

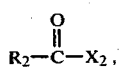

an alkali metal cyanide and an alkali metal borohydride.

In a preferred embodiment the process comprises forming a mixture of the acyl halides and a phase transfer catalyst in an inert water-immiscible solvent; bringing the mixture into contact with an aqueous solution of an alkali metal borohydride and an alkali metal cyanide; and maintaining the contact at a temperature and for a time sufficient to convert at least a portion of the acyl halides to cyanohydrin ester.

The acyl halides represented by the formulae:

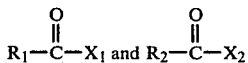

are independently selected from the group consisting of compounds represented by the general formula:

wherein R represents an alkyl, alkenyl, cycloalkyl, aryl, aralkyl, alkylphenyl, diphenyl ether, or polyphenyl radical, or a radical made up of any combination thereof; and may contain an inert substituent selected from the group consisting of halogen, alkyl and alkoxy; the radical having a total number of carbon atoms ranging from 1 to about 30; and X represents either a bromide or chloride radical.

The acyl halides represented by

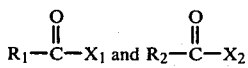

may, of course, be the same or different.

Preferably the compound represented by

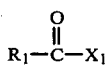

is meta-phenoxybenzoyl chloride, i.e.;

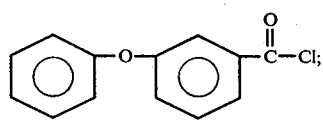

the compound represented by the formula

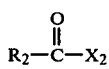

is 3-(2,2-dichlorovinyl)-2,2-dimethyl cyclopropane carboxylic acid chloride, i.e.,

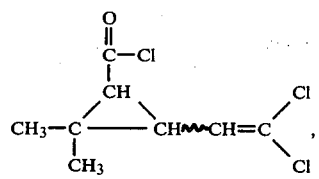

the alkali metal cyanide is sodium cyanide, and the alkali metal borohydride is sodium borohydride.

Although not critical to the practice of the present invention, it is preferred that the compounds represented by

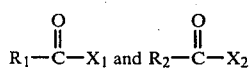

be used in equimolar quantities.

The alkali metal borohydrides used in the practice of the present invention include sodium borohydride, potassium borohydride, lithium borohydride and mixtures thereof; although sodium borohydride is preferred, because it is readily available.

About 0.25 equivalents of alkali metal borohydride is required to react with the acyl halides, since all four hydrogens on the alkali metal borohydride are active. On the other hand, the amount of alkali metal borohydride present in the reaction mixture should not exceed about 0.5 equivalents, as amounts in excess of about 0.5 equivalents can result in the formation of alcohols rather than cyanohydrin esters.

In the event that the acyl halide being used contains an acid, such as HCl, some of the alkali metal borohydride may be consumed by the acid and must be compensated for. Care must be exercised, however, that the total amount of alkali metal borohydride present in the reaction mixture does not exceed about 0.5 equivalents at any one time.

A preferred alternative is to purify the acyl halide prior to use to remove the acid, thereby obviating the necessity of adding alkali metal borohydride in excess of the actual amount required to react with the acyl halide.

Yet another alternative is to add small amounts of alkali metal borohydride or other base, such as sodium bicarbonate or sodium hydroxide to the acyl halide reaction mixture to neutralize the acid. If the alkali metal borohydride is used for this purpose, care must be exercised that the amount present does not exceed 0.5 equivalents at any one time. Then the amount of alkali metal borohydride needed to react with the acyl halide (i.e., about 0.25 equivalents based on the total amount of acyl halide present) may be safely added.

The phase transfer catalysts which are employed when the process of the present invention is practiced under conditions of phase transfer catalysis can be any of those which are generally used for phase transfer reactions. These include, but are not limited to, quaternary ammonium salts which are soluble in both the aqueous and organic phases, such as
benzyl trimethyl ammonium chloride,
tetra-n-butyl ammonium bromide,
tetra-n-butyl ammonium iodide and
tetra-n-hexyl ammonium bromide;
although tetra-n-butyl ammonium bromide and tetra-n-butyl ammonium iodide are preferred; with tetra-n-butyl ammonium bromide being most preferred. Other types of phase transfer catalysts may also be used.

The amount of phase transfer catalyst used ranges from about 0.005% to about 1.0% by weight of water-immiscible solvent used; although amounts ranging from about 0.1% to about 0.3% by weight of solvent are preferred.

The alkali metal cyanides which are reacted with acyl halides in the practice of the present invention include, but are not limited to sodium cyanide, potassium cyanide, and lithium cyanide. The preferred alkali metal cyanides are sodium cyanide and potassium cyanide, although sodium cyanide is most preferred. The amount of alkali metal cyanide used in the practice of the present invention is at least the stoichiometric equivalent of the total amount of acyl halides used. The amount of alkali metal cyanide used generally ranges from about 1 to about 3 or more equivalents of the acyl halides used, although preferably it ranges from about 1.05 to about 1.5 equivalents.

There are many solvents known in the art which can be used as the inert water-immiscible solvents when practicing the invention under conditions of phase transfer catalysis. These include, but are not limited to methylene chloride and other halogenated hydrocarbons; aliphatic hydrocarbons, aromatic hydrocarbons and ether solvents; although methylene chloride is preferred.

The relative amount of water-immiscible solvent used is not critical but it is generally preferred that the mixtures of acyl halide and water-immiscible solvent contain total concentrations of acyl halide ranging from about 5% to about 50% by weight of mixture.

The mixture of acyl halides, phase transfer catalyst and water-immiscible solvent is formed using conventional techniques. This mixture can be prepared by bringing the components together and stirring until a uniform mixture is formed.

In a similar manner, an aqueous solution of alkali metal borohydride and alkali metal cyanide, containing from about 2% to about 5% alkali metal borohydride and from about 10% to about 20% alkali metal cyanide by weight of solution, can be prepared by adding the proper amount of alkali metal borohydride and alkali metal cyanide to the proper amount of water and stirring until a uniform solution is formed.

At alkali metal borohydride concentrations above this range, the acyl halides can be reduced to alcohols, while at lower alkali metal borohydride concentrations an incomplete reaction can result. At alkali metal cyanide concentrations below the stated range the reaction may not go to completion and the unreacted acyl halides could be reduced to alcohols by the alkali metal borohydrides present. High concentrations of alkali metal cyanide, while of no particular benefit, will not be harmful.

The aqueous alkali metal borohydride/alkali metal cyanide solution and the mixture of acyl halides, phase transfer catalyst and water-immiscible solvents are then brought into contact with each other under such conditions as will promote a phase transfer reaction involving the acyl halides, phase transfer catalyst, alkali metal cyanide and alkali metal borohydride. This can generally be accomplished by intimately mixing the mixture and solution to form a reaction mixture.

Once the reaction mixture is formed, the phase transfer reaction will take place. This reaction is exothermic and external cooling may be required.

The reaction temperature should be maintained below about 50° C. as at temperatures in excess of about 50° C. an alcohol product can result instead of the desired cyanohydrin ester. A preferred temperature range is from about 20° C. to about 40° C.

The essential completion of the reaction will be indicated by the disappearance of the characteristic acid chloride carbonyl absorption band in the infrared spectrum. The conversion of the acyl halides to cyanohydrin ester will range from about 60 mol percent to about 100 mol percent.

The water-immiscible phase is then separated from the reaction mixture, and the solvent evaporated to yield the cyanohydrin ester product.

In an especially preferred embodiment, the present invention comprises a process for preparing an insecticidally active cyanohydrin ester which comprises reacting a mixture of meta-phenoxybenzoyl chloride and 3-(2,2-dichlorovinyl)-2,2-dimethyl cyclopropane carboxylic acid chloride with sodium cyanide and sodium borohydride by a phase transfer reaction in the presence of a phase transfer catalyst to form a cyanohydrin ester product of the meta-phenoxybenzoyl chloride and 3-(2,2-dichlorovinyl)-(2,2-dimethyl)cyclopropane carboxylic acid chloride.

This especially preferred embodiment is illustrated as follows:

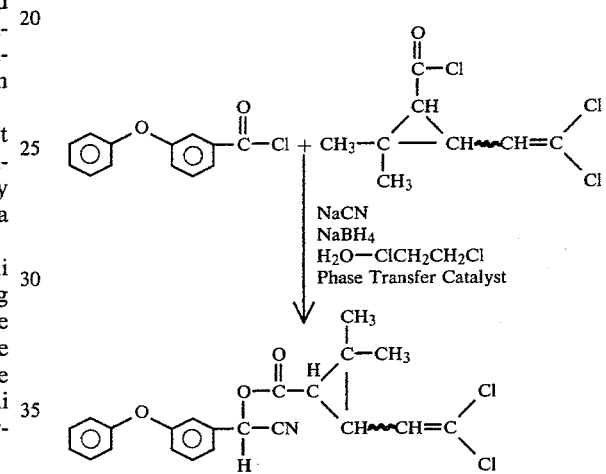

In order that the present invention be more fully understood, the following examples are given by way of illustration, no specific details or enumerations contained therein should be construed as limitations except insofar as they appear in the appended claims. All parts and percentages are by weight unless otherwise specifically designated.

EXAMPLE I

Preparation of Para-Tolualdehyde Cyanohydrin Para-Toluate

Water, in the amount of 40 milliliters, was added to a magnetically-stirred flask followed by 10.0 grams (0.204 mole) sodium cyanide, 0.65 gram (0.0171 mole) sodium borohydride and 0.15 gram of tetra-n-butyl ammonium bromide. To this was then added a solution of 15.5 g (0.10 mole) para-toluyl chloride in 150 milliliters of methylene chloride. After about ten minutes the temperature of the flask contents had risen from the initial ambient temperature to 32° C.

Infrared analysis of a sample taken fifty minutes after the two solutions were brought together indicated the presence of two carbonyl compounds: the cyanohydrin ester ($\nu_{c=o}$ 1730 cm$^{-1}$) and acyl cyanide ($\nu_{c=o}$ 1680 cm$^{-1}$). A solution of 0.10 gram (0.0026 mole) sodium borohydride in 5 milliliters of water was then added, and stirring was continued for an additional period of 70 minutes. The flask contents were then permitted to settle, after which the organic layer was separated from the aqueous layer. The organic layer was dried over magnesium sulfate, filtered and concentrated on a rotary evaporator to yield 12.2 grams of cyanohydrin ester (92% of theory).

The product was identical in spectral properties to a sample of authentic cyanohydrin ester prepared by acylation of para-tolualdehyde cyanohydrin with para-toluyl chloride.

EXAMPLE II

Preparation of R,S-α-Cyano-3-Phenoxybenzyl-(Cis, Trans)-3-(2,2-Dichlorovinyl)-2,2-Dimethyl Cyclopropane Carboxylate A solution of 2.34 grams (0.010 mole) of meta-phenoxybenzoyl chloride and 2.28 grams (0.010 mole) of dichlorochrysanthemyl chloride in ten milliliters of methylene chloride was added to a magnetically stirred flask containing a solution of 1.1 gram (0.0204 mole) of sodium cyanide, 0.13 gram (0.00342 mole) of sodium borohydride and 0.080 gram of tetra-n-butyl ammonium bromide in six milliliters of water, under ambient conditions.

The flask contents were stirred for 2.5 hours after which the flask contents were permitted to settle.

The organic layer was removed, dried over magnesium sulfate, filtered and concentrated on a rotary evaporator to yield 3.2 grams of cyanohydrin ester product; ir $\nu_{c=o}$ 1740 cm$^{-1}$. The product demonstrated LD$_{50}$ against black bean aphid, German cockroach and tobacco budworm of 0.0002, 0.006 and 0.0004 respectively compared to values of 0.0001, 0.002 and 0.0001 respectively for authentic R,S-α-cyano-3-phenoxybenzyl-(cis, trans)-3-(2,2-dichlorovinyl)-2,2-dimethyl cyclopropane carboxylate.

It will thus be seen that the present invention provides a process by which cyanohydrin esters can be prepared directly from acyl halides.

The objects set forth above, among those made apparent from the preceding description are, therefore, effectively attained and, since certain changes may be made in the above method without departure from the scope of the invention, it is intended that all matter contained in the above description shall be interpreted as illustrative and not in a limiting sense.

What is claimed is:

1. A process for preparing cyanohydrin esters represented by the formula:

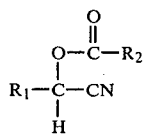

which comprises reacting an alkali metal cyanide and an alkali metal borohydride with at least one acyl halide represented by the structure:

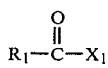

and at least one acyl halide represented by the structure:

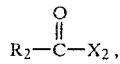

wherein $R_1$ and $R_2$ can be the same or different, and each represents an alkyl, alkenyl, cycloalkyl, aryl, aralkyl alkylphenyl, diphenyl ether, or polyphenyl radical, or a radical made up of any combination thereof; and may contain an inert substituent selected from the group consisting of halogen, alkyl and alkoxy; the radical having a total number of carbon atoms ranging from 1 to about 30; and $X_1$ and $X_2$ each independently represent a bromide or chloride radical.

2. The method of claim 1 wherein said alkali metal borohydride is sodium borohydride, potassium borohydride, lithium borohydride or any combination thereof.

3. The method of claim 2 wherein said alkali metal borohydride is sodium borohydride.

4. The method of claim 3 wherein said reaction is achieved by contacting a mixture of said acyl halides, a phase transfer catalyst and a water-immiscible solvent with an aqueous solution of said alkali metal cyanide and alkali metal borohydride.

5. The method of claim 4 wherein said phase transfer catalyst is tetra-n-butyl ammonium bromide.

6. The method of claim 5 wherein said water-immiscible solvent is methylene chloride.

7. The method of claim 6 wherein said acyl halide represented by the structural formula:

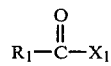

is meta-phenoxybenzoyl chloride, and said acyl halide represented by the structural formula:

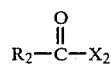

is 3-(2,2-dichlorovinyl)-2,2-dimethyl cyclopropane carboxylic acid chloride.

8. A process for preparing cyanohydrin esters which comprises forming a first mixture of an acyl chloride represented by the structural formula:

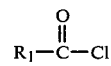

and an acyl chloride represented by the structural formula:

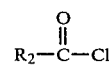

wherein $R_1$ and $R_2$ can be the same or different and each represents an alkyl, alkenyl, cycloalkyl, diphenyl ether, polyphenyl radical or a radical made up of any combination thereof, having a total number of carbon atoms ranging from 1 to about 30; a phase transfer catalyst and a water-immiscible solvent, wherein the total amount of said acyl chloride in said mixture ranges from about 5% to about 50% by weight mixture and the total amount of said phase transfer catalyst ranges from about 0.005% to about 1.0% by weight of said water-immiscible solvent;

bringing said first mixture into contact with an aqueous solution of an alkali metal cyanide and an alkali metal borohydride and maintaining said contact at a temperature and for a time sufficient to convert at least a portion of said acyl chlorides to the cyanohydrin ester product of said acyl chlorides.

9. A process for preparing an insecticidally-active cyanohydrin ester which comprises reacting a mixture of meta-phenoxybenzoyl chloride and 3-(2,2-dichlorovinyl)-2,2-dimethyl cyclopropane carboxylic acid chloride with sodium cyanide and sodium borohydride by a phase transfer reaction in the presence of a phase transfer catalyst to form a cyanohydrin ester product of said meta-phenoxybenzoyl chloride and 3-(2,2-dichlorovinyl)-2,2-dimethyl cyclopropane carboxylic acid chloride.

* * * * *